United States Patent
Saito

(10) Patent No.: US 9,585,819 B2
(45) Date of Patent: Mar. 7, 2017

(54) MOISTURIZING APPARATUS AND ELECTRICAL EQUIPMENT INCLUDING THE SAME, AND MOISTURIZING METHOD

(71) Applicant: Sharp Kabushiki Kaisha, Osaka-shi, Osaka (JP)

(72) Inventor: Emi Saito, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days.

(21) Appl. No.: 14/425,396

(22) PCT Filed: Sep. 11, 2013

(86) PCT No.: PCT/JP2013/074490
§ 371 (c)(1),
(2) Date: Mar. 3, 2015

(87) PCT Pub. No.: WO2014/042173
PCT Pub. Date: Mar. 20, 2014

(65) Prior Publication Data
US 2015/0250690 A1 Sep. 10, 2015

(30) Foreign Application Priority Data
Sep. 13, 2012 (JP) ................................. 2012-201733

(51) Int. Cl.
*A61K 8/22* (2006.01)
*A61H 33/12* (2006.01)
(Continued)

(52) U.S. Cl.
CPC ................ *A61K 8/22* (2013.01); *A45D 19/02* (2013.01); *A45D 19/16* (2013.01); *A45D 34/02* (2013.01);
(Continued)

(58) Field of Classification Search
CPC . A61K 8/22; A61K 8/19; A61K 8/046; A45D 19/16; A45D 19/02;
(Continued)

(56) References Cited

U.S. PATENT DOCUMENTS

| 3,947,659 A * | 3/1976 | Ono ........................ A45D 20/00 34/91 |
| 4,578,563 A * | 3/1986 | Eguchi .................... A45D 19/16 392/396 |

(Continued)

FOREIGN PATENT DOCUMENTS

| CN | 1406644 A | 4/2003 |
| JP | 2001-000497 A | 1/2001 |

(Continued)

OTHER PUBLICATIONS

Official Communication issued in International Patent Application No. PCT/JP2013/074490, mailed on Oct. 29, 2013.

*Primary Examiner* — Rachel Steitz
(74) *Attorney, Agent, or Firm* — Keating & Bennett, LLP

(57) ABSTRACT

A moisturizing apparatus includes an ion generating device, a mist generating device, and a control device. The ion generating device generates positive ions and negative ions bound to water molecules from the air by an electrical discharge in the atmosphere. The mist generating device reduces the liquid to fine particles in the form of mist and sprays the liquid in the form of mist. The moisturizing apparatus moisturizes the skin or hair, through combined use of application of ions from the ion generating device and spraying of the mist from mist generating device, toward the skin or hair.

9 Claims, 5 Drawing Sheets

(51) Int. Cl.
| | |
|---|---|
| *H01T 23/00* | (2006.01) |
| *A61N 1/44* | (2006.01) |
| *A45D 19/16* | (2006.01) |
| *A61K 8/19* | (2006.01) |
| *A61Q 5/00* | (2006.01) |
| *A61Q 19/00* | (2006.01) |
| *A45D 19/02* | (2006.01) |
| *A45D 34/02* | (2006.01) |
| *A45D 34/04* | (2006.01) |
| *H01T 19/04* | (2006.01) |
| *A45D 19/00* | (2006.01) |

(52) U.S. Cl.
CPC .............. A45D 34/04 (2013.01); A61H 33/12 (2013.01); A61K 8/19 (2013.01); A61N 1/44 (2013.01); A61Q 5/00 (2013.01); A61Q 19/00 (2013.01); H01T 23/00 (2013.01); *A45D 2019/0058* (2013.01); *A45D 2200/057* (2013.01); *A45D 2200/202* (2013.01); *A61H 2201/10* (2013.01); *A61H 2201/50* (2013.01); *A61H 2201/5043* (2013.01); *A61K 2800/805* (2013.01); *H01T 19/04* (2013.01)

(58) Field of Classification Search
CPC .... A45D 2019/0058; A45D 2019/0033; A45D 2019/0041; A45D 2019/025; A45D 2200/054; A45D 2200/057; A45D 2200/058; A45D 2200/202; A45D 2200/207; A45D 34/04; A45D 20/10; H01T 23/00; A61Q 5/00; A61Q 19/00; A61H 33/08; A61H 33/12; A61H 33/14; A61H 33/6047; A61H 33/6052; A61H 33/6057; A61H 2033/141; A61H 2033/145; A61H 2033/148; A61N 5/0616; A61N 5/0617; A61N 2005/0643; A61N 2005/0644; A61N 1/44
USPC ....... 132/200, 212, 271, 272, 317, 320, 333, 132/202, 210
See application file for complete search history.

(56) References Cited

U.S. PATENT DOCUMENTS

| | | | | |
|---|---|---|---|---|
| 4,941,068 | A * | 7/1990 | Hofmann | H01T 23/00 128/202.25 |
| 5,377,702 | A * | 1/1995 | Sakurai | A45D 44/00 132/271 |
| 5,805,406 | A * | 9/1998 | Mailand | A45D 20/12 361/212 |
| 6,176,977 | B1 * | 1/2001 | Taylor | B01D 53/32 123/539 |
| 6,584,985 | B2 * | 7/2003 | Omura | A45D 20/50 132/270 |
| 6,763,606 | B2 * | 7/2004 | Saida | A45D 20/00 34/96 |
| 6,907,888 | B2 * | 6/2005 | Saida | A46B 15/0022 132/116 |
| 6,923,794 | B2 * | 8/2005 | Ohmura | A45D 1/04 392/385 |
| 7,350,317 | B2 * | 4/2008 | Matsui | A45D 19/16 34/96 |
| 7,427,273 | B2 * | 9/2008 | Mitsui | A61H 23/0245 601/17 |
| 7,478,640 | B2 * | 1/2009 | Saida | A45D 1/04 132/228 |
| 8,448,649 | B2 * | 5/2013 | Kloeppel-Riech | A45D 20/12 132/148 |
| 8,545,419 | B2 * | 10/2013 | Kim | A45D 44/00 601/2 |
| 8,556,237 | B2 * | 10/2013 | Yamaguchi | A01N 3/00 261/142 |
| 2003/0055469 | A1 | 3/2003 | Ohmura | |
| 2003/0072675 | A1 * | 4/2003 | Takeda | A61L 9/22 422/22 |
| 2004/0118425 | A1 * | 6/2004 | Santhouse | A45D 4/16 132/233 |
| 2004/0128853 | A1 * | 7/2004 | Ura | A45D 19/16 34/96 |
| 2004/0129291 | A1 * | 7/2004 | Ura | A45D 19/16 132/272 |
| 2006/0214020 | A1 | 9/2006 | Suda et al. | |
| 2007/0019501 | A1 * | 1/2007 | Kiessl | A45D 19/16 366/144 |
| 2008/0023575 | A1 * | 1/2008 | Trumble | B05B 11/0037 222/135 |
| 2008/0097279 | A1 * | 4/2008 | Sugawara | A61H 33/14 604/20 |
| 2010/0212683 | A1 | 8/2010 | Mizuno | |
| 2010/0269849 | A1 * | 10/2010 | Ishikawa | A45D 1/06 132/271 |
| 2010/0288298 | A1 * | 11/2010 | Serresvives | A45D 1/04 132/272 |
| 2012/0267547 | A1 * | 10/2012 | Hafemann | A45D 20/12 250/424 |
| 2012/0302817 | A1 | 11/2012 | Nishiuchi et al. | |
| 2013/0158337 | A1 * | 6/2013 | Okano | A61L 2/14 600/1 |
| 2013/0184513 | A1 * | 7/2013 | Saito | A61N 5/10 600/1 |
| 2014/0060565 | A1 * | 3/2014 | Saito | A45D 20/12 132/200 |
| 2014/0298670 | A1 * | 10/2014 | Tahara | A45D 20/10 34/97 |

FOREIGN PATENT DOCUMENTS

| | | |
|---|---|---|
| JP | 2010-194127 A | 9/2010 |
| JP | 2011-005147 A | 1/2011 |
| JP | 2011-005266 A | 1/2011 |
| JP | 2011-098187 A | 5/2011 |

* cited by examiner

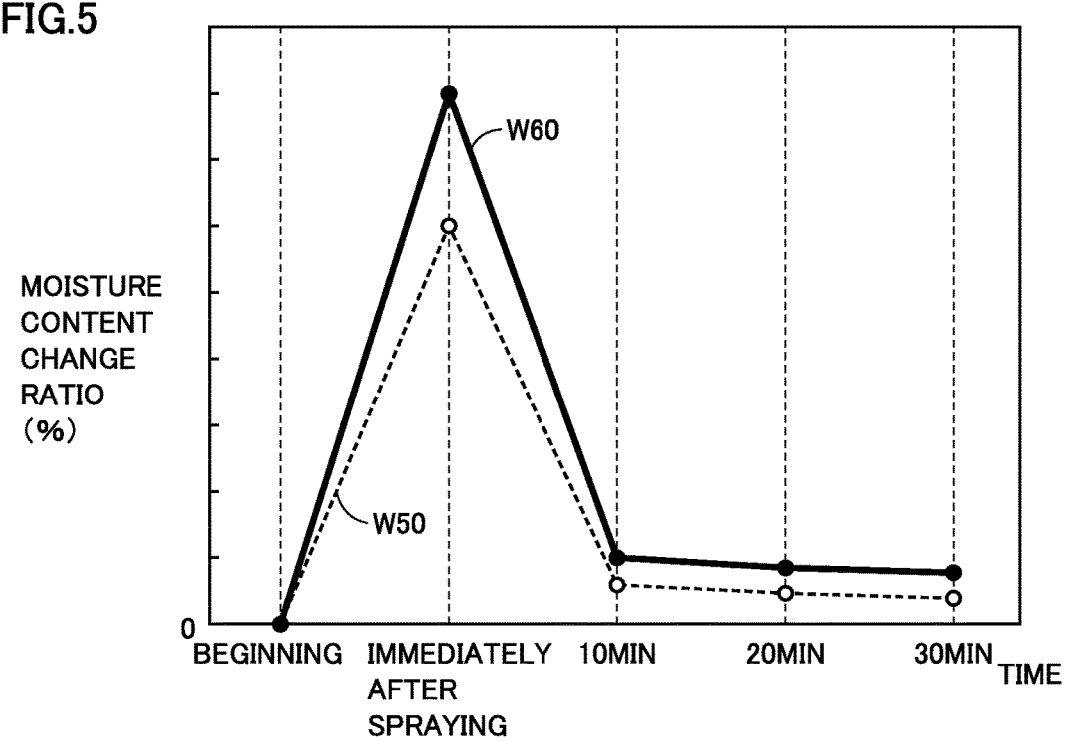

MOISTURIZING APPARATUS AND ELECTRICAL EQUIPMENT INCLUDING THE SAME, AND MOISTURIZING METHOD

TECHNICAL FIELD

The present invention relates to a moisturizing apparatus and electrical equipment including the moisturizing apparatus, as well as a moisturizing method. More specifically, the invention relates to a technique for improving a moisturizing effect for the skin or hair, through the combined use of ions and liquid mist.

BACKGROUND ART

Cosmetically, preventing the skin from becoming dry is an issue, and there is a desire to increase the moisture content in the skin.

In order to increase the skin moisture content, conventionally, preparations such as lotions containing moisturizing ingredients are commonly applied to the skin.

Further, the following techniques for increasing the skin moisture content are known. In Japanese Patent Laying-Open No. 2011-5266 (PTD 1), for example, the skin moisture content is increased by spraying, to the skin, water in the form of particles generated by condensation and atomization of moisture in the air. In Japanese Patent Laying-Open No. 2001-497 (PTD 2), for example, the skin moisture content is increased by spraying mist generated using an ultrasonic device to the skin.

CITATION LIST

Patent Document

PTD 1: Japanese Patent Laying-Open No. 2011-5266
PTD 2: Japanese Patent Laying-Open No. 2001-497

SUMMARY OF INVENTION

Technical Problem

According to the methods described in Japanese Patent Laying-Open No. 2011-5266 (PTD 1) and Japanese Patent Laying-Open No. 2001-497 (PTD 2), although the moisture content given to the skin can be temporarily increased, there is still room for improvement in terms of making the moisturizing effect last longer.

The present invention was made to solve the aforementioned problem, and an object of the invention is to provide a moisturizing method and a moisturizing apparatus allowing a higher moisturizing effect to be achieved.

Solution to Problem

A method for improving a function of moisturizing the skin or hair according to the invention improves the function of moisturizing the skin or hair, through combined use of application of positive ions and negative ions generated from the air by an electrical discharge in the atmosphere using an ion generating device, and spraying of a liquid in the form of mist generated using a mist generating device, toward the skin or hair.

Preferably, the method improves the function of moisturizing the skin or hair by applying the positive ions and the negative ions after spraying of the liquid in the form of mist.

Preferably, the method improves the function of moisturizing the skin or hair by applying the positive ions and the negative ions during and after spraying of the liquid in the form of mist.

Preferably, the method improves the function of moisturizing the skin or hair either by applying the positive ions and the negative ions during spraying of the liquid in the form of mist, or by applying the positive ions and the negative ions after spraying of the liquid in the form of mist.

Preferably, the positive ions are $H^+(H_2O)_m$, where m is any natural number, and the negative ions are $O_2^-(H_2O)_n$, where n is zero or any natural number.

A moisturizing apparatus for moisturizing the skin or hair according to the invention includes an ion generating device configured to generate positive ions and negative ions bound to water molecules from the air by an electrical discharge in the atmosphere, and a mist generating device configured to reduce the liquid to fine particles in the form of mist and sprays the liquid in the form of mist. Application of the positive ions and the negative ions from the ion generating device is combined with spraying of the liquid in the form of mist from the mist generating device, toward the skin or hair.

Preferably, the moisturizing apparatus further includes a control device configured to control the ion generating device and the mist generating device. After spraying of the liquid in the form of mist, the control device causes spraying of the liquid to stop, and causes the positive ions and the negative ions to be applied.

Preferably, the moisturizing apparatus further includes a control device configured to control the ion generating device and the mist generating device. During and after spraying of the liquid in the form of mist, the control device causes the positive ions and the negative ions to be applied.

Preferably, the moisturizing apparatus further includes a control device configured to control the ion generating device and the mist generating device. The control device can operate the ion generating device and the mist generating device in any of a first operation mode and a second operation mode. In the first operation mode, the positive ions and the negative ions can be applied during spraying of the liquid in the form of mist. In the second operation mode, the positive ions and the negative ions can be applied after spraying of the liquid in the form of mist.

Preferably, any of the ion generating device and the mist generating device is configured to be removable.

Electrical equipment according to the invention includes the moisturizing apparatus described above.

Advantageous Effects of Invention

With the moisturizing method and the moisturizing apparatus according to the invention, a moisturizing effect higher than conventionally obtained can be achieved.

BRIEF DESCRIPTION OF DRAWINGS

FIG. 5 is a second diagram showing results of an experiment for comparison between the moisturizing method according to the embodiment of the invention and the moisturizing method according to the conventional technique.

DESCRIPTION OF EMBODIMENTS

Figure 1:
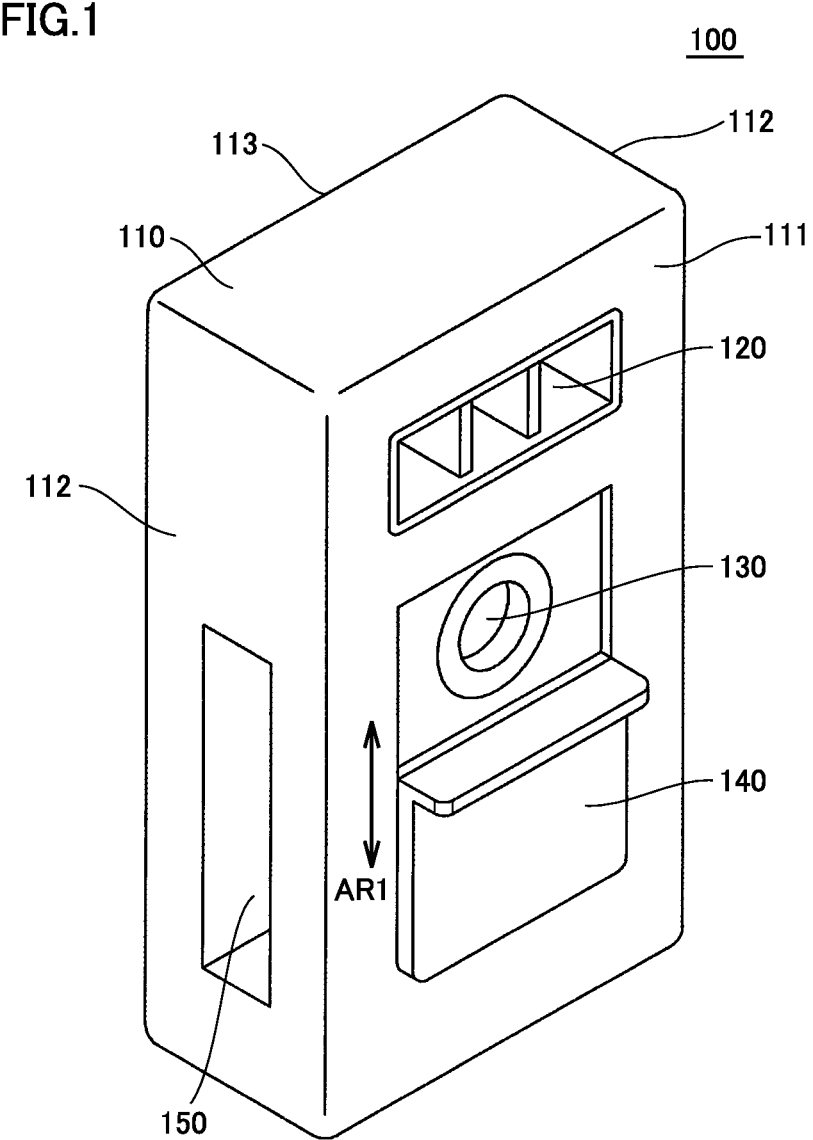
FIG. 1 is a schematic diagram of a moisturizing apparatus according to an embodiment of the invention.

Embodiments of the present invention will be described in detail below with reference to the drawings, in which the same or corresponding elements are designated by the same reference characters, and description thereof will not be repeated.

[Description of Configuration of Moisturizing Apparatus]

Figure 2:
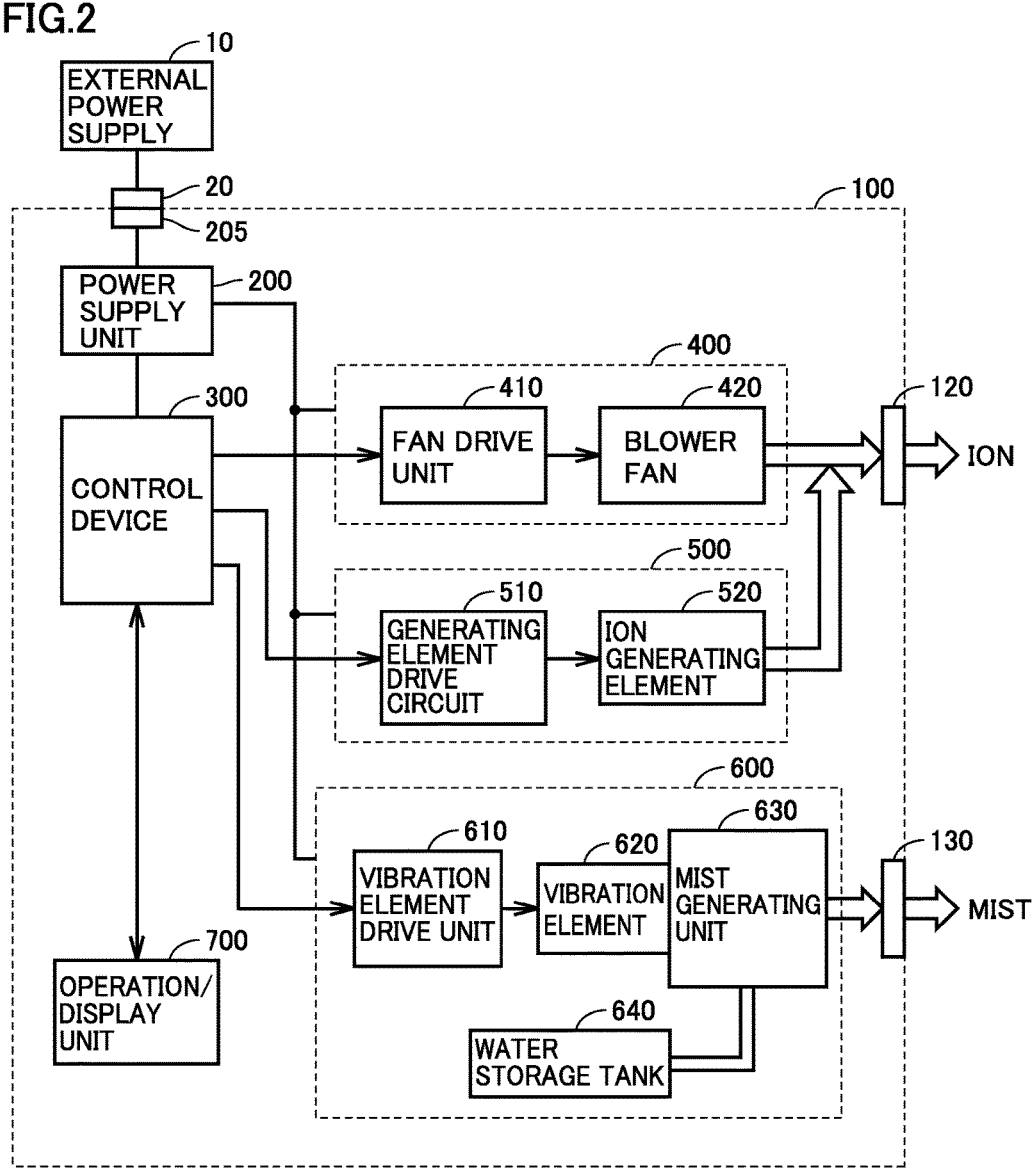
FIG. 2 is an overall function block diagram of the moisturizing apparatus shown in FIG. 1.

With reference to FIGS. 1 and 2, the configuration of a moisturizing apparatus according to an embodiment of the invention will be described. FIG. 1 shows a schematic diagram of moisturizing apparatus 100 according to the embodiment of the invention. FIG. 2 shows a functional block diagram for explaining a detailed function of moisturizing apparatus 100 shown in FIG. 2.

With reference to FIG. 1, moisturizing apparatus 100 includes a housing 110, an ion discharge port 120, a mist discharge port 130, a cover 140, and an air suction port 150.

Housing 110 is formed in a substantially rectangular parallelepiped, and accommodates various devices contained in moisturizing apparatus 100 described below with FIG. 2.

Ion discharge port 120 is arranged on a main face 111 of housing 110 having a large width. Ions generated at an ion generating device 500 described below with FIG. 2 are discharged through ion discharge port 120.

Mist discharge port 130 is arranged on the same main face 111 as ion discharge port 120. A liquid in the form of mist generated at mist generating device 600 described with FIG. 2 is discharged through mist discharge port 130.

Mist discharge port 130 includes cover 140 that can be opened and closed by a user's operation. Cover 140 is movable in the direction of arrow head AR1 shown in FIG. 1, for example. Cover 140 is put in a closed position when moisturizing apparatus 100 is not in use, or when mist is not generated by mist generating device 600.

Air suction port 150 is formed on a side face 112 of housing 110. Air suction port 150 serves to draw air from outside into the housing when a blower fan 420 described below with FIG. 2 is operated. The air drawn from air suction port 150 is guided to ion discharge port 120 through blower fan 420. This causes ions generated by ion generating device 500 to be discharged through ion discharge port 120.

Note that air suction port 150 may also be provided on a rear face 113 instead of, or in addition to, side face 112 of housing 110.

Next, moisturizing apparatus 100 will be described in detail with FIG. 2. With reference to FIG. 2, moisturizing apparatus 100 includes, in addition to the elements described with FIG. 1, a power supply unit 200, a control device 300, a blower mechanism 400, ion generating device 500, mist generating device 600, and an operation/display unit 700

Power supply unit 200 receives power from an external power supply 10 transmitted from a power connector 20, which is connected to a power receiving unit 205. Power supply unit 200 then distributes the received power, and supplies driving power to control device 300, blower mechanism 400, ion generating device 500, and mist generating device 600. Note that when moisturizing apparatus 100 is operated with power from a power storage device (not shown) incorporated therein, power supply unit 200 distributes the power from the power storage device to control device 300, blower mechanism 400, ion generating device 500, and mist generating device 600.

Blower mechanism 400 includes a fan drive unit 410 and blower fan 420. Fan drive unit 410 is a drive device for driving a fan motor (not shown) contained in blower fan 420. Fan drive unit 410 drives blower fan 420 based on an instruction from control device 300.

Ion generating device 500 includes a generating element drive circuit 510 and ion generating element 520. Generating element drive circuit 510 is a circuit for applying voltage to a high-voltage circuit contained in ion generating element 520, based on an instruction from control device 300. A detailed configuration and a principle of ion generation of ion generating device 500 will be described below with FIG. 3.

Ion generating element 520 is formed along a path of air flow leading to ion discharge port 120 from blower fan 420. This causes ions generated by ion generating element 520 to be delivered to ion discharge port 120, and the ions are discharged out of moisturizing apparatus 100 through ion discharge port 120.

Mist generating device 600 includes a vibration element drive unit 610, a vibration element 620, a mist generating unit 630, and a water storage tank 640.

Mist generating device 600 according to this embodiment is described by way of example as being configured to reduce a liquid to fine particles to form mist by ultrasonic vibrations. Mist generating device 600, however, is not limited to this configuration, and any other known technique can be used so long as a liquid can be reduced to mist.

Vibration element drive unit 610 is a drive circuit for causing vibration element 620 to vibrate at high frequency. Vibration element 620 has a probe that ultrasonically vibrates, and includes mist generating unit 630 that covers a head surface of this probe with a fine mesh (not shown).

A liquid stored in water storage tank 640 (for example, pure water, a cosmetic, a quasi drug, or a drug) is supplied to an inner side of the mesh of mist generating unit 630. The liquid supplied is forced toward an outer side from the inner side of the mesh by ultrasonic vibrations of vibration element 620. When the liquid passes through this mesh, it is decomposed into fine particles to generate mist. The mist generated is discharged to the outside through mist discharge port 130.

Note that mist generating device 600 may be fixed on housing 110, or may be configured to be separable from housing 110. Alternatively, ion generating device 500 may be configured to be separable from housing 110.

Operation/display unit 700 is an interface for receiving an operation signal through the user's operation, and notifying the user of information. Operation/display unit 700 is configured to include, for example, an operation instrument such as a switch and a display instrument such as an LED or a liquid crystal panel. Operation/display unit 700 transmits the received operation signal from the user to control device 300, and displays notification information transmitted from control device 300 to the user.

Control device 300 controls blower mechanism 400, ion generating device 500, and mist generating device 600, based on the user's setting, operation, and the like.

Figure 3:
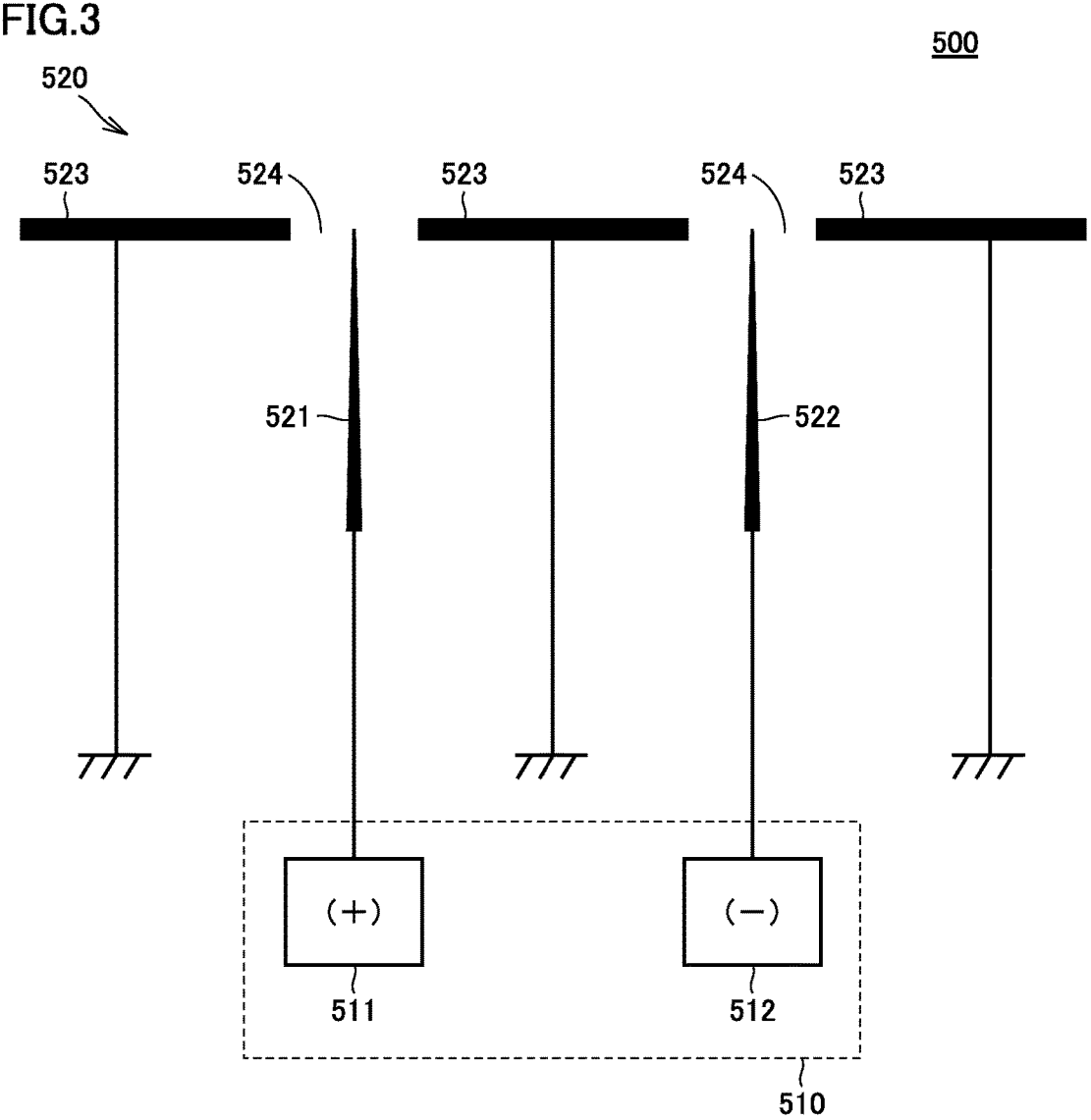
FIG. 3 is a diagram for explaining a principle of ion generation by an ion generating device.

FIG. 3 is a diagram for explaining a detailed configuration and a principle of ion generation of ion generating device 500 shown in FIG. 2.

With reference to FIGS. 2 and 3, generating element drive circuit 510 includes high-voltage generating devices 511, 512. Ion generating element 520 includes voltage-application needle electrodes 521, 522 and ground electrodes 523.

Voltage-application needle electrodes 521, 522 are ion generating electrodes each having a needle-like tip, and are connected to high-voltage generating devices 511, 512, respectively.

Ground electrodes 523 are arranged adjacent to voltage-application needle electrodes 521, 522. Ground electrodes 523 each have a through-hole 524 corresponding to voltage-application needle electrode 521 or 522, allowing to pass the voltage-application needle electrode therethrough.

Voltage-application needle electrodes 521, 522 are each arranged such that they are substantially centrally positioned in through-hole 524 of each ground electrode 523, and their needle-like tip falls within a range of thicknesses of each ground electrode 523 in through-hole 524.

High-voltage generating device 511 applies a positive DC pulse voltage to voltage-application needle electrode 521. This causes a corona discharge between voltage-application needle electrode 521 and ground electrode 523, causing the air around voltage-application needle electrode 521 to be positively ionized. Specifically, $H^+(H_2O)_m$, where m is any natural number, is produced as positive ions.

On the other hand, high-voltage generating device 512 applies a negative DC pulse voltage to voltage-application needle electrode 522. This causes a corona discharge between voltage-application needle electrode 522 and ground electrode 523, causing the air around voltage-application needle electrode 522 to be negatively ionized. Specifically, $O_2^-(H_2O)_n$, where n is zero or any natural number, is produced as negative ions.

The positive ions and negative ions generated are carried by the wind blown from blower fan 420 to be discharged into the atmosphere through ion discharge port 120.

Note that the number (concentration) of ions generated varies depending on the size and the pulse period of the DC pulse voltage applied by each of the high-voltage generating devices, and is controlled by control device 300. The number of ions generated may be fixed, or may be variable depending on the user's setting or mode.

As described above, moisturizing apparatus 100 according to this embodiment sprays the liquid in the form of mist generated by mist generating device 600, and further applies ions generated by ion generating device 500, toward the skin and/or hair. This allows an increase in the skin moisture content due to moisture supplied as the mist, and allows a further increase in the skin moisture content because the skin surface is locally hydrophilized by the ions to incorporate therein water molecules in the air. Consequently, the moisturizing effect for the skin and/or hair can be improved.

Note that moisturizing apparatus 100 has a first operation mode in which it applies ions while spraying the liquid in the form of mist, and a second operation mode in which it sprays the liquid in the form of mist for a predetermined time, and then stops spraying of the mist and applies ions. The operation mode can be switched appropriately between these two operation modes, in accordance with the user's operation or setting of operation/display unit 700 shown in FIG. 2. For example, the operation mode may be switched between the first operation mode and the second operation mode by the user's manual operation, or may be automatically switched between the first operation mode and the second operation mode, in response to a predetermined condition such as time or the like being established. Alternatively, the mist may be intermittently sprayed while application of ions is continued.

While the foregoing description has shown case where the moisturizing apparatus is used as an independent apparatus, the function of the moisturizing apparatus may be incorporated into other electrical equipment (for example, facial equipment such as a steamer, a dryer, or a moisturizing machine for indoor use).

The following describes results of experiments on effects obtained with the moisturizing apparatus according to this embodiment, in comparison with effects obtained according to a comparative example.

[Description of Verification Experiment]

<Verification Experiment 1>

In verification experiment 1, temporal changes in the moisture content in the skin were measured for a subject, with respect to the following four cases where: (1) no treatment was performed; (2) spraying of the mist only was performed; (3) the application of ions only was performed; and (4) ions were applied after spraying of the mist.

The inner side of the left front arm of the subject was tested as a test portion. A mark was provided around the center of the inner side of the left front arm. The mist was sprayed and/or ions were applied toward the mark as a target.

The subject rested while sitting on a chair for 15 minutes in a room at a room temperature of 23±3° C. and a humidity of 21±2%. Then, mist of pure water was sprayed toward the above-mentioned test portion, and immediately after the spraying, ions were applied for 60 minutes.

The mist was sprayed toward the test portion from a position 20 cm away from the skin. Ions were applied at a position 50 cm away from the test portion, with the ion generating device and the blower mechanism being adjusted such that the ion concentration of each of positive ions and negative ions would be $100000/cm^3$. Note that in order to equalize the condition of the wind from the blower mechanism, blowing of air only was performed with the same blower mechanism also in the case where ions were not applied.

The skin moisture content was measured as follows. A skin moisture content before spraying of the mist was used as an initial value, and measurements were taken at three points around the mark provided on the test portion every 20 minutes of spraying of the mist. An average value of the measurement values at the three points was evaluated as a change ratio. Note that the measurement of the skin moisture content was performed with a moisture meter that measures a moisture content on the skin surface (keratin).

Figure 4:
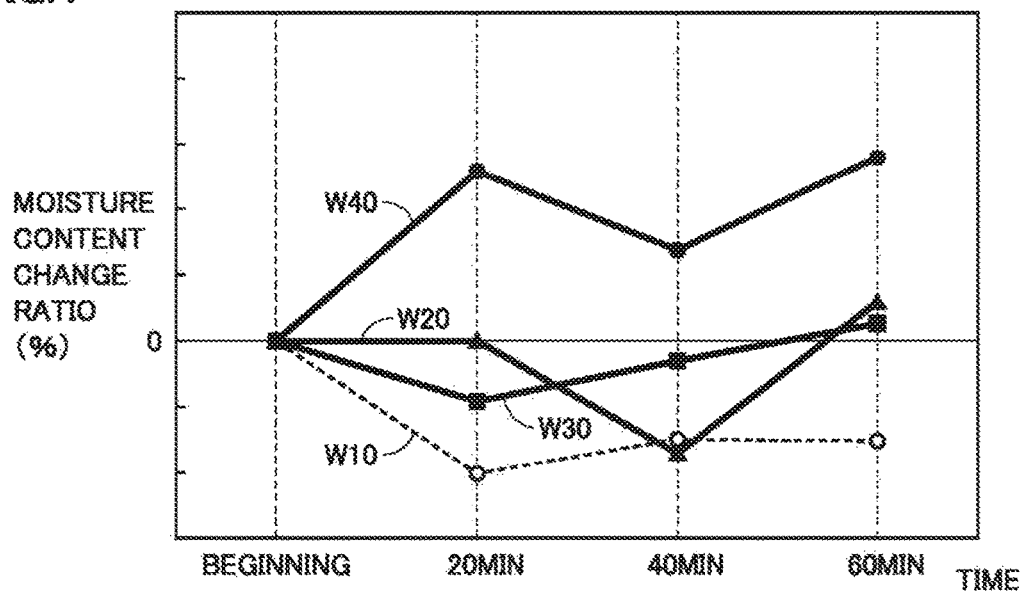
FIG. 4 is a first diagram showing results of an experiment for comparison between the moisturizing method according to the embodiment of the invention and a moisturizing method according to a conventional technique.

FIG. 4 is a graph showing results measured under the conditions as described above. In the graph, the horizontal axis represents time, and the vertical axis represents the moisture content change ratio with respect to the skin moisture content in the initial state before spraying of the mist. In FIG. 4, curve W10 represents the case where no treatment was performed, curve W20 represents the case where spraying of the mist only was performed, curve W30 represents the case where the application of ions only was performed, and curve W40 represents the case where ions were applied after spraying of the mist. Note that when spraying of the mist is performed, the moisture content becomes extremely high immediately after spraying of the mist, with great measurement variations. In the graph of FIG. 4, therefore, data obtained immediately after spraying of the mist is excluded.

According to the graph of FIG. 4, it is concluded that in the case where spraying of the mist was combined with the application of ions (W40), the moisture content change ratio is greater than in any other cases, and the highest moisturizing effect of all the other cases is obtained.

Further, the moisture content change ratio in the case where spraying of the mist was combined with the application of ions (W40) is even greater than a sum of the moisture content change ratio in the case where spraying of the mist only was performed (W20) and the moisture content change ratio in the case where the application of ions only was performed (W30). One reason therefor is believed to be that in addition to the moisture content alone given by each of spraying of the mist and the application of ions, the evaporation of the sprayed mist is suppressed by the application of ions.

Note that although not shown in the graph, a lotion with a higher moisturizing effect was also used instead of pure water as a liquid for use as the mist, and in this case also, it was concluded that as in FIG. 4, the case where spraying of the mist was combined with the application of ions achieved a moisturizing effect higher than those obtained in the other cases.

<Verification Experiment 2>

In the above-described verification experiment 1, a comparison was made in terms of moisturizing effect in the case where spraying of the mist was performed and then stopped, and then ions were applied.

In verification experiment 2, a comparison was made in terms of moisturizing effect in the case where ions were applied simultaneously while the mist was sprayed, and the application of ions was continued after stopping the spraying of the mist.

In verification experiment 2, temporal changes in the moisture content in the skin were measured for three subjects, with respect to the following two cases where: (1) ions were applied during and after spraying of the mist; and (2) spraying of the mist only was performed.

As in verification experiment 1, the inner side of the left front arm of each subject was used as the test portion. A mark was provided around the center of the inner side of the left front arm. The mist was sprayed and/or ions were applied toward the mark as a target.

Each subject rested while sitting on a chair for 15 minutes in a room at a room temperature of 24.5±1° C. and a humidity of 20±2%. Then, mist of a lotion was sprayed toward the above-mentioned test portion, and immediately after the spraying, ions were applied for 30 minutes. Here, the phrase "immediately after the spraying" of the mist refers to 30 seconds after spraying of the mist.

The mist was sprayed toward the test portion from a position 10 cm away from the skin. Ions were applied at a position 50 cm away from the test portion, with the ion generating device and the blower mechanism adjusted such that the ion concentration of each of positive ions and negative ions would be 100000/cm$^3$. Note that in order to equalize the condition of the wind from the blower mechanism, blowing of air only was performed with the same blower mechanism also in the case where ions were not applied.

A commercially available lotion sold for use as mist was used as the lotion used in the experiment. Major ingredients contained in the lotion were water, DPG (dipropylglycol), BG (Butylene Grycol), glycerol, sucrose, trehalose, caffeine, sorbitol, EDTA-2Na, tocopherol acetate, *Saccharomyces* lysate extract, *Centella asiatica* extract, *Anthemis nobilis* flower extract, yeast extract, aloe vera leaf water, phenoxyethanol, chlorphenesin, benzoic acid Na, benzoic acid, and sorbic acid.

The skin moisture content was measured as follows. A skin moisture content before spraying of the mist was used as an initial value, and ions were applied simultaneously with the start of spraying of the mist. Measurements were taken at three points around the mark provided on the test portion every 10 minutes after stopping the spraying of the mist. An average value of the measurement values at the three points was evaluated as a change ratio. Note that the measurement of the skin moisture content was performed with a moisture meter that measures a moisture content on the skin surface (keratin).

FIG. 5 is a graph showing results measured under the conditions as described above. In the graph, the horizontal axis represents time, and the vertical axis represents the moisture content change ratio with respect to the skin moisture content in the initial state before spraying of the mist. In FIG. 5, curve W50 represents the case where spraying of the mist only was performed, and curve W60 represents the case where the application of ions and spraying the mist were performed.

According to the graph of FIG. 5, it is concluded that in the case where the mist was sprayed while ions were applied (W60), the moisture content change ratio immediately after spraying of the mist is greater than the case where spraying of the mist only was performed (W50), and thus, a high moisturizing effect was obtained.

Further, compared to the case where spraying of the mist only was performed, the state having a high moisturizing effect is maintained even after 30 minutes after spraying of the mist, and therefore, higher durability of the moisturizing effect was confirmed. One reason therefor is believed to be that when spraying of the mist and the application of ions are performed simultaneously, ions are adsorbed to the moisturizing ingredients contained in the mist, which allows more efficient hydration of the skin.

Using the moisturizing apparatus as described above, a moisturizing effect higher than conventionally obtained can be achieved through combined use of spraying of the mist and the application of ions toward the skin and/or hair.

The foregoing description has shown by way of example the case of using the moisturizing apparatus as shown in FIGS. 1 and 2 into which the mist spraying function and the ion application function are integrated. However, the moisturizing method according to the invention is not limited to using such an integrated apparatus. Specifically, the moisturizing method of the invention is also applicable to the case where spraying of the mist and the application of ions are combined by using a mist generating device and an ion generation device individually.

It should be understood that the embodiments disclosed herein are illustrative and non-restrictive in every respect. It is intended that the scope of the present invention is defined by the terms of the claims rather than by the foregoing description, and includes all modifications within the scope and meaning equivalent to the claims.

REFERENCE SIGNS LIST

10: external power supply; 20: power connector; 100: moisturizing apparatus; 110: housing; 111: main face; 112: side face; 113: rear face; 120: ion discharge port; 130: mist discharge port; 140: cover; 150: air suction port; 200: power supply unit; 205: power receiving unit; 300: control device; 400: blower mechanism; 410: fan drive unit; 420: blower fan; 500: ion generating device; 510: generating element drive circuit; 511, 512: high-voltage generating device; 520: ion generating element; 521, 522: voltage-application needle electrode; 523: ground electrode; 524: through-hole; 600: mist generating device; 610: vibration element drive unit; 620: vibration element; 630: mist generating unit; 640: water storage tank; 700: display unit.

The invention claimed is:

1. A method of moisturizing skin or hair comprising:
    applying positive ions and negative ions generated from the air by an electrical discharge in the atmosphere using an ion generating device; and
    spraying of a liquid in the form of mist generated using a mist generating device, toward the skin or hair, wherein
    said positive ions and said negative ions are applied simultaneously after the spraying of said liquid in the form of mist.

2. The method according to claim 1, wherein
    said positive ions and said negative ions are applied during and after spraying of said liquid in the form of mist.

3. The method according to claim 1, wherein
    said positive ions are $H^+(H_2O)_m$, where m is any natural number, and
    said negative ions are $O_2^-(H_2O)_n$, where n is zero or any natural number.

4. A moisturizing apparatus for moisturizing the skin or hair, comprising:
    an ion generating device configured to generate positive ions and negative ions bound to water molecules from the air by an electrical discharge in the atmosphere;
    a mist generating device configured to reduce a liquid to fine particles in the form of mist and spray the liquid in the form of mist; and
    a control device configured to control said ion generating device and said mist generating device, wherein
    application of said positive ions and said negative ions from said ion generating device is combined with spraying of said liquid in the form of mist from said mist generating device, toward the skin or hair, and
    said control device is configured to control said mist generating device and said ion generating device to automatically stop spraying of said liquid after a predetermined time, and to automatically start the simultaneous application of said positive ions and said negative ions after the spraying of said liquid is stopped.

5. The moisturizing apparatus according to claim 4, wherein
    during and after spraying of said liquid in the form of mist, said control device causes said positive ions and said negative ions to be applied.

6. The moisturizing apparatus according to claim 4, wherein
    said control device is further configured to operate said ion generating device and said mist generating device in any of a first operation mode and a second operation mode,
    in said first operation mode, said positive ions and said negative ions are applied during spraying of said liquid in the form of mist, and
    in said second operation mode, said positive ions and said negative ions are applied after spraying of said liquid in the form of mist.

7. The moisturizing apparatus according to claim 4, wherein
    said positive ions are $H^+(H_2O)_m$, where m is any natural number, and
    said negative ions are $O_2^-(H_2O)_n$, where n is zero or any natural number.

8. The moisturizing apparatus according to claim 4, wherein
    said ion generating device and said mist generating device is configured to be separable from the moisturizing apparatus.

9. Electrical equipment comprising:
    the moisturizing apparatus according to claim 4; wherein
    the electrical equipment is a steamer, a dryer, or a moisturizing machine.

\* \* \* \* \*